(12) United States Patent
Klapötke et al.

(10) Patent No.: US 9,296,664 B2
(45) Date of Patent: Mar. 29, 2016

(54) ENERGETIC ACTIVE COMPOSITION COMPRISING A DIHYDROXYLAMMONIUM SALT OR DIAMMONIUM SALT OF A BISTETRAZOLEDIOL

(75) Inventors: Thomas M. Klapötke, München (DE); Niko Fischer, Augsburg (DE); Dennis Fischer, Dinkelscherben (DE); Davin G. Piercey, Edmonton (CA); Jörg Stierstorfer, Wörthsee (DE); Marius Reymann, Schlegelsberg (DE)

(73) Assignee: LUDWIG-MAXIMILLIANS- UNIVERSITAET MUENCHEN, Munich (DE)

( * ) Notice: Subject to any disclaimer, the term of this patent is extended or adjusted under 35 U.S.C. 154(b) by 0 days.

(21) Appl. No.: 14/239,481

(22) PCT Filed: Aug. 16, 2012

(86) PCT No.: PCT/EP2012/066023
§ 371 (c)(1),
(2), (4) Date: Feb. 18, 2014

(87) PCT Pub. No.: WO2013/026768
PCT Pub. Date: Feb. 28, 2013

(65) Prior Publication Data
US 2014/0171657 A1 Jun. 19, 2014

Related U.S. Application Data

(60) Provisional application No. 61/568,760, filed on Dec. 9, 2011.

(30) Foreign Application Priority Data

Aug. 19, 2011 (DE) .......................... 10 2011 081 254
Dec. 8, 2011 (DE) .......................... 10 2011 120 745

(51) Int. Cl.
*C06B 49/00* (2006.01)
*C07D 257/04* (2006.01)

(52) U.S. Cl.
CPC .............. *C06B 49/00* (2013.01); *C07D 257/04* (2013.01)

(58) Field of Classification Search
None
See application file for complete search history.

(56) References Cited

U.S. PATENT DOCUMENTS 6,040,453 A 3/2000 Hyoda et al.
2013/0071658 A1* 3/2013 Nomura .................... C09J 7/02
428/355 R

FOREIGN PATENT DOCUMENTS

EP 2 377 840 A2 10/2011
WO WO 2011/118506 * 3/2011 ............. C09J 201/00

OTHER PUBLICATIONS

Fischer et al., J. Mater. Chem., 2012, 22, 20418-20422, Published online Aug. 9, 2012.*
English translation for the Written Opinion of the International Searching Authority for International Application No. PCT/EP2012/066023, dated Oct. 29, 2012.
Sućeska, Muhamed, "Calculation of Detonation Parameters by EXPLO5 Computer Program," Materials Science Forum, 2004, vols. 465-466, pp. 325-330.
Sućeska, Muhamed, "EXPLO5—Computer Program for Calculation of Detonation Parameters," Proc. of 32nd Int. Annual Conference of ICT, Jul. 3-6, Karlsruhe, German, 2001, pp. 110/1-110/11.
Göbel et al., "Nitrotetrazolate-2N-oxides and the Strategy of N-Oxide Introduction," Journal of the American Chemical Society, Nov. 11, 2010, vol. 132, No. 48, pp. 17216-17226.
Hobbs et al., "Calibrating the BKW-EOS with a Large Product Species Data Base and Measured C—J Properties," Proc. of the 10th Symp. (International) on Detonation, ONR 33395-12, Jul. 12-16, 1993, pp. 409-418.
International Search Report issued in PCT/EP2012/066023, mailed Oct. 29, 2012.
Sućeska, Muhamed, "Calculation of the Detonation Properties of C—H—N—O Explosives," Propellants, Explosives, Pyrotechnics, 1991, vol. 16, pp. 197-202.
Sućeska, Muhamed, "Evaluation of Detonation Energy from EXPLO5 Computer Code Results," Propellants, Explosives, Pyrotechnics, 1999, vol. 24, pp. 280-285.
Tselinskii et al., "Synthesis and Reactivity of Carbohydroximoyl Azides: I. Aliphatic and Aromatic Carbohydroximoyl Azides and 5-Substituted 1-Hydroxytetrazoles Based Thereon," Russian Journal of Organic Chemistry, 2001, vol. 37, No. 3, pp. 430-436.
Written Opinion issued in PCT/EP2012/066023, mailed Oct. 29, 2012.

* cited by examiner

*Primary Examiner* — Alicia L Otton
(74) *Attorney, Agent, or Firm* — Birch, Stewart, Kolasch & Birch, LLP

(57) ABSTRACT

The invention relates to an energetic active composition comprising a dihydroxylammonium salt or diammonium salt of 5,5'-bistetrazole-1,1'-diol, 5,5'-bistetrazole-1,2'-diol or 5,5'-bistetrazole-2,2'-diol or a mixture of at least two of these salts.

20 Claims, 3 Drawing Sheets

Figure 1:
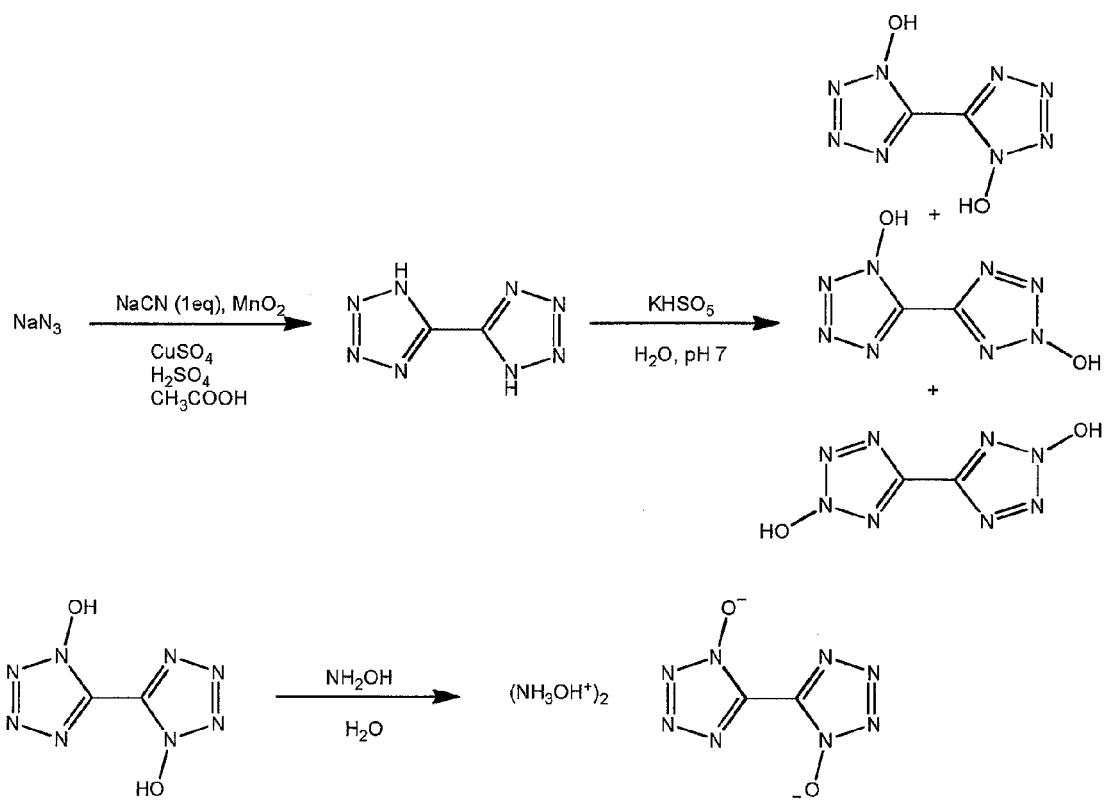

ENERGETIC ACTIVE COMPOSITION COMPRISING A DIHYDROXYLAMMONIUM SALT OR DIAMMONIUM SALT OF A BISTETRAZOLEDIOL

CROSS REFERENCE TO RELATED APPLICATIONS

This application is the National Phase of PCT/EP2012/066023 filed on Aug. 16, 2012, which claims priority under 35 U.S.C. §119(e) to U.S. Provisional Application No. 61/568,760 filed on Dec. 9, 2011, under 35 U.S.C §119(a) to Patent Application No. 10 2011 081 254.7 filed in Germany on Aug. 19, 2011, and under 35 U.S.C §119(a) to Patent Application No. 10 2011 120 745.0 filed in Germany on Dec. 8, 2011, all of which are hereby expressly incorporated by reference into the present application.

The invention relates to an energetic active composition comprising a dihydroxylammonium salt or diammonium salt of a bistetrazolediol, to a use of the dihydroxylammonium salt or diammonium salt, to a process for preparing the dihydroxylammonium salt or diammonium salt, and to bistetrazolediols and also dihydroxylammonium salts and diammonium salts thereof.

U.S. Pat. No. 6,040,453 A discloses a process for preparing the diammonium salt of 5,5'-bi-1H-tetrazole using dicyan, sodium azide, ammonium chloride, and water as reaction medium. The process sees the dicyan added at low temperature to an aqueous solution comprising sodium azide and ammonium chloride. The mixture is subsequently heated. The 5,5'-bi-1H-tetrazole diammonium salt that is formed in this process is precipitated in the form of crystals that are of low solubility.

In Russian Journal of Organic Chemistry, volume 37, No. 3, 2001, pages 430 to 436, Tselinskii I. V. et al. disclose the synthesis and reactivity of aliphatic and aromatic carbohydroximoyl azides and of 5-substituted 1-hydroxytetrazoles based thereon.

Known from Göbel, M. et al., J. AM. CHEM. SOC. 2010, 132, pages 17216 to 17226 is the oxidation of nitrotetrazolate to give the nitrotetrazolate-2N-oxide anion, and the preparation of the hydroxylammonium salt thereof. In the theoretical calculation, the hydroxylammonium salt showed better detonation characteristics than the secondary explosive HMX. According to page 17224, left-hand column, second paragraph of the publication, however, the thermal stability of the salt and the extreme deliquescence of the free acid, which dissolves in absorbed water within a few minutes in air, likely rules out any practical application.

Additionally known as secondary explosives are nitramines, such as hexogen (RDX), octogen (HMX), or hexanitroisowurtzitane (CL-20), for example. One disadvantage of these nitramines and their reaction products after detonation lies in their toxicity and environmental impact. Additionally there is a need for more powerful secondary explosives. Such explosives are in fact already known, in the form of dinitroazofuroxane or octanitrocubane, for example. A disadvantage of these compounds lies in their sensitivity, which is high in comparison to other secondary explosives. Their synthesis, additionally, is very complex and requires 10 or more reaction steps.

It is an object of the present invention to provide an alternative energetic active composition which is easy to prepare and combines high powerfulness with safe handling and acceptable environmental impact. The intention additionally is to provide constituents of the active composition, a use of at least one constituent of this active composition, and a process for preparing such a constituent, and to specify compounds suitable as starting materials or intermediates for the production of such a constituent.

The object of the invention is achieved by means of the features of items 1, 2, 3 and 15 to 20 below. Useful embodiments of the invention are evident from the features of items 4 to 14 below.

1. An energetic active composition comprising a dihydroxylammonium salt or diammonium salt of 5,5'-bistetrazole-1,1'-diol, 5,5'-bistetrazole-1,2'-diol, or 5,5'-bistetrazole-2,2'-diol, or a mixture of at least two of these salts.

2. The use of a dihydroxylammonium salt or diammonium salt of 5,5'-bistetrazole-1,1'-diol, 5,5'-bistetrazole-1,2'-diol, or 5,5'-bistetrazole-2,2'-diol, or a mixture of at least two of these salts, as explosive.

3. A process for preparing a dihydroxylammonium salt or diammonium salt of 5,5'-bistetrazole-1,1'-diol, 5,5'-bistetrazole-1,2'-diol, or 5,5'-bistetrazole-2,2'-diol, or a mixture of at least two of these salts, with the following steps:
   a) oxidizing 5,5'-bistetrazole to give a mixture of 5,5'-bistetrazole-1,1'-diol, 5,5'-bistetrazole-1,2'-diol, and 5,5'-bistetrazole-2,2'-diol, or promoting the isomerization of diazidoglyoxime to 5,5'-bistetrazole-1,1'-diol or a 5,5'-bistetra-zole-1,1'-diolate,
   b) incubating the reaction product obtained according to step a) with hydroxylamine, hydroxylammonium ions, ammonium ions, or ammonia in aqueous solution, and
   c) isolating the resultant precipitate.

4. The process as disclosed in item 3, wherein the oxidizing according to step a) takes place by addition, more particularly addition in excess, of $2KHSO_5 \cdot KHSO_4 \cdot K_2SO_4$ or of another inorganic or organic peroxo acid or hypofluorous acid or another oxygen transfer agent to the 5,5'-bistetrazole.

5. The process as disclosed in item 3 or 4, wherein the oxidizing takes place in an aqueous solution buffered to a pH of between 5 and 8, more particularly between 7 and 7.5.

6. The process as disclosed in any of items 3 to 5, wherein the reaction product obtained in step a) by oxidizing of 5,5'-bistetrazole is acidified and subsequently extracted with an organic extractant, more particularly ether, and thereafter recovered from the extract, more particularly by evaporation, the reaction product being subsequently optionally recrystallized, more particularly from methanol.

7. The process as disclosed in any of items 3 to 6, wherein, in step a), 5,5'-bistetrazole is oxidized and the aqueous solution, after the precipitation of the dihydroxylammonium salt or diammonium salt of 5,5'-bistetrazole-1,1'-diol, more particularly with addition of further hydroxylamine or ammonia or of the hydroxylammonium ions or ammonium ions, is concentrated by evaporation, where either as a result at least the solubility product of the dihydroxyammonium salt or diammonium salt of 5,5'-bistetrazole-1,2'-diol or 5,5'-bistetrazole-2,2'-diol is exceeded, and so the dihydroxylammonium salt or diammonium salt precipitates, or the dihydroxylammonium salt or diammonium salt is obtained from the residue resulting from the evaporation by recrystallization, more particularly from an ethanol/water mixture.

8. The process as disclosed in item 3, wherein the promoting of the isomerization takes place by acylation, more particularly by means of acetyl chloride, or by incubation with gaseous HCl, more particularly in ether as solvent or in an ether-comprising solvent.

9. The process as disclosed in item 3 or 8, wherein the diazidoglyoxime is produced by reaction of dichloroglyoxime with an azide, the dichloroglyoxime being produced more particularly by reaction of glyoxime with chlorine, the glyoxime being produced more particularly by reaction of glyoxal with hydroxylamine.

10. The process as disclosed in item 9, wherein the reaction of the dichloroglyoxime with the azide takes place in a nonaqueous solvent, more particularly dimethylformamide (DMF) or N-methyl-2-pyrrolidone (NMP), the solvent with the resultant diazidoglyoxime being subsequently mixed with the ether and incubated with the gaseous HCl.

11. The process as disclosed in item 10, wherein before step c) the ether and the HCl, more particularly with addition of $H_2O$ which then likewise requires evaporative removal, are evaporated off and, where present, the DMF is evaporated off, and so, in the case of DMF as solvent, a mixture of dimethylammonium 5,5'-bistetrazole-1,1'-diolate and a 5,5'-bistetrazole-1,1'-diolate which comprises at least one counterion of the azide, and in the case of NMP as solvent a residue comprising 5,5'-bistetrazole-1,1'-diol, is obtained.

12. The process as disclosed in item 11, wherein the dimethylammonium 5,5'-bistetrazole-1,1'-diolate is dissolved in $H_2O$ and subsequently a hydroxylammonium salt, more particularly hydroxylammonium chloride, is added, and so the dihydroxylammonium salt of 5,5'-bistetrazole-1,1'-diol is obtained as the precipitate.

13. The process as disclosed in item 11, wherein the residue comprising 5,5'-bistetrazole-1,1'-diol is taken up in an aqueous alkali hydroxide solution and the precipitating alkali 5,5'-bistetrazole-1,1'-diolate is isolated and dissolved in $H_2O$, with subsequent addition of a hydroxylammonium salt, more particularly hydroxylammonium chloride, and so the dihydroxylammonium salt of 5,5'-bistetrazole-1,1'-diol is obtained as the precipitate.

14. The process as disclosed in item 12 or 13, wherein an ammonium salt, more particularly ammonium chloride, is added instead of the hydroxylammonium salt, and so the diammonium salt of 5,5'-bistetrazole-1,1'-diol is obtained as the precipitate.

15. 5,5'-Bistetrazole-1,2'-diol.

16. 5,5'-Bistetrazole-2,2'-diol.

17. The dihydroxylammonium salt of 5,5'-bistetrazole-1,2'-diol.

18. The dihydroxylammonium salt of 5,5'-bistetrazole-2,2'-diol.

19. The diammonium salt of 5,5'-bistetrazole-1,2'-diol.

20. The diammonium salt of 5,5'-bistetrazole-2,2'-diol.

Provided in accordance with the invention is an energetic active composition which comprises a dihydroxylammonium salt or diammonium salt of 5,5'-bistetrazole-1,1'-diol, 5,5'-bistetrazole-1,2'-diol, or 5,5'-bistetrazole-2,2'-diol, or a mixture of at least two of these salts. An energetic active composition here refers to an active composition which reacts detonatively or deflagratively after its ignition. This composition may be an active pyrotechnic composition. An advantage of the stated dihydroxylammonium salts and diammonium salts is that the compounds in question are not nitramines and hence that no environmentally impactful nitrosamines are formed during their breakdown in the environment, either. The environmental compatibility of these salts is much better than the environmental compatibility of the stated nitramines and of the reaction products of the nitramines.

It has emerged, furthermore, that the dihydroxylammonium salt dihydroxylammonium 5,5'-bistetrazole-1,1'-diolate, for example, has a calculated detonation velocity which is higher by 250 m/s than that of CL-20 and higher by 700 m/s than that of RDX. The diammonium salt diammonium 5,5'-bistetrazole-1,1'-diolate has a detonation velocity similar to that of RDX. Both salts therefore meet the preconditions required for a high-performance explosive. The detonation velocities were calculated using the program EXPLO5, version 5.05 (M. Sućeska, EXPLO5.04 program, Zagreb, Croatia, 2011; M. Sućeska, Calculation of detonation parameters by EXPLO5 computer program, *Materials Science Forum*, 2004, 465-466, 325-330; M. Sućeska, Calculation of the detonation properties of C—H—N—O explosives, *Propellants, Explos., Pyrotech.* 1991, 16, 197-202; M. Sućeska, Evaluation of detonation energy from EXPLO5 computer code results, *Propellants, Explos., Pyrotech.* 1999, 24, 280-285, M. L. Hobbs, M. R. Baer, *Proc. Of the $10^{th}$ Symp. (International) on Detonation*, ONR 33395-12, Boston, Mass., July 12-16, 1993, p. 409).

The sensitivity of dihydroxylammonium 5,5'-bistetrazole-1,1'-diolate and of diammonium 5,5'-bistetrazole-1,1'-diolate, additionally, is lower in each case than that of RDX. The impact sensitivity as determined by the drop hammer method is 7.5 J for RDX, meaning that RDX for use as secondary explosive has to be desensitized by addition of binders and plasticizers in order to be amenable to handling. Even without additives, in contrast, the dihydroxylammonium salt of 5,5'-bistetrazole-1,1'-diol (hereinafter: "TKX50") has a much lower impact sensitivity, of 20 J. Without additives, indeed, the diammonium salt of 5,5'-bistetrazole-1,1'-diol (hereinafter: "ABTOX") has an impact sensitivity of 35 J. Consequently TKX50 and ABTOX are much safer to handle than RDX, and permit easier compliance with the prescribed requirements for insensitive munitions.

The density of TKX50, furthermore, is higher than the density of RDX, and an active composition comprising TKX50 can have a much higher density than an active composition comprising RDX, owing to a low fraction of additives necessary for desensitization. This means that within a given volume it is possible to accommodate a higher mass of a TKX50-comprising active composition and so to achieve a higher performance than with RDX.

The density of ABTOX corresponds approximately to the density of RDX. ABTOX, furthermore, has an outstanding thermal stability. At a heating rate of 5° C./min, it decomposes only at a temperature of 290° C. and therefore far exceeds the decomposition temperature of RDX. ABTOX is therefore suitable for use at a high ambient temperature, at which RDX cannot be used.

The properties of TKX50 and ABTOX in comparison to 2,4,6-trinitrotoluene (2,4,6-TNT), RDX, β-HMX, and ε-CL-20 are set out in the table below:

|  | 2,4,6-TNT | RDX | β-HMX | ε-CL20 | TKX50 | ABTOX |
|---|---|---|---|---|---|---|
| Formula | $C_7H_5N_3O_6$ | $C_3H_6N_6O_6$ | $C_4H_8N_8O_8$ | $C_6H_6N_{12}O_{12}$ | $C_2H_8N_{10}O_4$ | $C_2H_8N_{10}O_2$ |
| Molecular weight [g $mol^{-1}$] | 227.1 | 222.1 | 296.2 | 438.2 | 236.2 | 204.2 |
| IS [J][a] | 15 | 7.5 | 7 | 4 | 20 | 35 |
| FS [N][b] | 353 | 120 | 112 | 48 | 120 | 360 |

-continued

|  | 2,4,6-TNT | RDX | β-HMX | ε-CL20 | TKX50 | ABTOX |
|---|---|---|---|---|---|---|
| ESD test [J][c] | — | 0.2 | 0.2 | — | 0.1 | 0.25 |
| N [%][d] | 18.5 | 37.8 | 37.8 | 38.3 | 59.3 | 68.6 |
| Ω [%][e] | −74.0 | −21.6 | −21.6 | −11.0 | −27.1 | −47.0 |
| $T_{dec.}$ [° C.][f] | 290 | 210 | 285 | 195 | 221 | 290 |
| Density [g cm$^{-3}$][g] | 1.713 | 1.858 | 1.944 | 2.083 | 1.918 | 1.800 |
| $\Delta_f U°$/kJ kg$^{-1}$[h] | −168 | 489 | 493 | 919 | 2006 | 1576 |
| $\Delta_E U°$/kJ kg$^{-1}$[i] | 5258 | 6190 | 6185 | 6406 | 6025 | 4195 |
| $T_E$ [K][j] | 3663 | 4232 | 4185 | 4616 | 3954 | 2931 |
| $P_{C-J}$ [kbar][k] | 235 | 380 | 415 | 467 | 424 | 316 |
| D [m s$^{-1}$][l] | 7459 | 8983 | 9221 | 9445 | 9698 | 8809 |
| Gas volume [L kg$^{-1}$][m] | 569 | 734 | 729 | 666 | 846 | 843 |

[a]Impact sensitivity (measured by the drop hammer method of the Bundesanstalt für Materialforschung und -prüfung, 1 of 6);
[b]friction sensitivity (measured with a friction apparatus according to the Bundesanstalt für Materialforschung und -prüfung, 1 of 6);
[c]measured with the electrostatic discharge device from the company OZM Research s.r.o., Czech Republic;
[d]nitrogen content;
[e]oxygen balance;
[f]decomposition temperature by DSC (Differential Scanning Calorimetry) measurement (5° C. per minute);
[g]determined by x-ray diffractometry at about 100K;
[h]energy of formation, calculated by the CBS-4M method;
[i]explosion energy;
[j]explosion temperature;
[k]detonation pressure;
[l]detonation velocity;
[m]determined on the assumption of exclusively gaseous reaction products.

A further advantage of the salts encompassed by the active composition of the invention is that the final step in their synthesis can take place in an aqueous solution and as a result is relatively safe. From water or the aqueous solution, the salts crystallize in ideal blocklike crystals. These crystals are advantageous for the formulation of active compositions, since the low surface area/volume ratio of the blocks, relative to the needles which typically form with other explosive compounds, means that less plasticizer and binder are needed in order to provide an active substance amenable to safe handling. As a result, a higher content of explosive compound in the active composition, and hence a higher performance, are achieved. Moreover, the relatively low water-solubility of the salts is advantageous for their further processing.

In a test of the performance using the SSSRT (Small Scale Shock Reactivity Test), which examines the extent to which a block of aluminum buckles on detonation of an explosive under investigation, it was found that the performance of TKX50 following ignition thereof is similar to that of β-HMX and higher than that of RDX. The performance of ABTOX in the SSSRT was lower than that of RDX, owing to only partial detonation. The only partial detonation shows that ABTOX is very safe to handle, since its complete detonation requires a booster explosive.

Since it is known that explosive compounds which are less sensitive in the SSSRT require a greater amount in order to exhibit their performance, and more sensitive explosives with a relatively low performance exhibit an apparently higher performance, it can be assumed that the actual performances of TKX50 and ABTOX outstrip the performance of β-HMX.

The dihydroxylammonium salt of 5,5'-bistetrazole-2,2'-diol has a somewhat lower thermal stability than TKX50, but like TKX50, it has a relatively high density. The high density is a decisive criterion for powerful secondary explosives. The dihydroxylammonium salt of 5,5'-bistetrazole-2,2'-diol has a higher sensitivity than TKX50 and is therefore suitable not only as a secondary explosive but also as a booster explosive. A booster explosive is an explosive which serves to intensify the effect of another explosive, and whose sensitivity and amenability to initiation are lower by comparison with a primary explosive and higher by comparison with a secondary explosive.

That the stated dihydroxylammonium salts and diammonium salts would have such advantageous properties could not have been expected. According to Göbel, M. et al., J. AM. CHEM. SOC. 2010, 131, page 17224, left-hand column, second paragraph, the thermal stability and the extreme deliquescence of the free acid likely rule out any practical application. For the salt investigated in that publication, namely the hydroxylammonium salt of nitrotetrazolate 2N-oxide, the decomposition temperature was only 157° C. Given the fact that tests had shown anhydrous 5,5'-bistetrazole-1,1'-diol to be relatively unstable and to be almost impossible to handle safely as an explosive because of high sensitivity toward impact, friction, and electrostatic discharge, the skilled person could not have assumed that the dihydroxylammonium salts and diammonium salts encompassed by the active composition of the invention would have such outstanding qualities as explosives.

The invention further relates to the use of a dihydroxylammonium salt or diammonium salt of 5,5'-bistetrazole-1,1'-diol, 5,5'-bistetrazole-1,2'-diol, or 5,5'-bistetrazole-2,2'-diol or a mixture of at least two of these salts as explosive, more particularly as secondary explosive. The sensitivity of the dihydroxylammonium salt of 5,5'-bistetrazole-2,2'-diol has proved high enough to allow it to be used, indeed, as a booster explosive.

The invention additionally relates to a process for preparing a dihydroxylammonium salt or diammonium salt of 5,5'-bistetrazole-1,1'-diol, 5,5'-bistetrazole-1,2'-diol, or 5,5'-bistetrazole-2,2'-diol, or a mixture of at least two of these salts, with the following steps:
  a) oxidizing 5,5'-bistetrazole to give a mixture of 5,5'-bistetrazole-1,1'-diol, 5,5'-bistetrazole-1,2'-diol, and 5,5'-bistetrazole-2,2'-diol, or
     promoting the isomerization of diazidoglyoxime to 5,5'-bistetrazole-1,1'-diol or a 5,5'-bistetrazole-1,1'-diolate, b) incubating the reaction product obtained according to step a) with hydroxylamine, hydroxylammonium ions, ammonium ions, or ammonia in aqueous solution, and c) isolating the resultant precipitate.

The reaction product obtained according to step a) may be the mixture according to step a) or the 5,5'-bistetrazole-1,1'-diol. The oxidizing according to step a) may be accomplished by addition of $2KHSO_5 \cdot KHSO_4 \cdot K_2SO_4$ or of another inorganic or organic peroxo acid or hypofluorous acid, or another oxygen transfer agent, to the 5,5'-bistetrazole. $2KHSO_5 \cdot KHSO_4 \cdot K_2SO_4$ is sold under the trade name "Oxone" by the company DuPont. The addition of Oxone or of the other inorganic or organic peroxo acid or hypofluorous acid, or of the other oxygen transfer agent, takes place preferably in excess, in order to ensure complete oxidation of the 5,5'-bistetrazole. When Oxone is used in excess, the stated mixture is formed with a marked excess of 5,5'-bistetrazole-2,2'-diol. Oxidizing takes place preferably in an aqueous solution buffered to a pH of between 5 and 8, more particularly between 7 and 7.5. The buffering may be done, for example, using trisodium phosphate. At the stated pH, the 5,5'-bistetrazole is predominantly in deprotonated form. As a result, a nucleophilic attack by the 5,5'-bistetrazole on the peroxomonosulfate, which is necessary for oxidation by Oxone, is favored.

To increase the purity of the reaction product, the reaction product obtained in step a) by oxidizing of 5,5'-bistetrazole can be acidified and subsequently extracted with an organic extractant, more particularly ether. The ether stated here and hereinafter is more particularly diethyl ether. The reaction product may thereafter be obtained from the extract, more particularly by evaporation. To increase the purity further, the residue which remains after evaporation may be recrystallized. Methanol has proven a particularly suitable solvent for this purpose.

The dihydroxylammonium salt and the diammonium salt of 5,5'-bistetrazole-1,1'-diol have emerged as being markedly less soluble in water than are the dihydroxylammonium salts and diammonium salts of 5,5'-bistetrazole-1,2'-diol and 5,5'-bistetrazole-2,2'-diol. In order to precipitate specifically the dihydroxylammonium salt or diammonium salt of 5,5'-bistetrazole-1,1'-diol from the mixture formed by oxidizing, comprising 5,5'-bistetrazole-1,1'-diol, 5,5'-bistetrazole-1,2'-diol, and 5,5'-bistetrazole-2,2'-diol, the different solubilities of the dihydroxylammonium salts and diammonium salts that can be precipitated from the mixture mean that it is necessary only to add the hydroxylamine or ammonia to the aqueous solution.

For precipitation of the dihydroxylammonium salts and diammonium salts of 5,5'-bistetrazole-1,2'-diol and 5,5'-bistetrazole-2,2'-diol, the aqueous solution, after the precipitation of the dihydroxylammonium salt or diammonium salt of 5,5'-bistetrazole-1,1'-diol, more particularly with addition of further hydroxylamine or ammonia or of the hydroxylammonium ions or ammonium ions, can be concentrated by evaporation. By this means it is possible to exceed at least the solubility product of the dihydroxylammonium salt or diammonium salt of 5,5'-bistetrazole-1,2'-diol or 5,5'-bistetrazole-2,2'-diol, and so the dihydroxylammonium salt or diammonium salt is precipitated. Alternatively, the dihydroxylammonium salt or diammonium salt may be obtained from the residue resulting from the evaporation, by recrystallization, more particularly from an ethanol/water mixture.

Since oxidizing 5,5'-bistetrazole produces the 5,5'-bistetrazole-1,1'-diol in only a small amount in relation to the 5,5'-bistetrazole-2,2'-diol, it has emerged as being advantageous to promote the isomerization of diazidoglyoxime to bistetrazole-1,1'-diol, since in that case no 5,5'-bistetrazole-1,2'-diol and no 5,5'-bistetrazole-2,2'-diol is formed. The isomerization may be promoted by acylation, more particularly by means of acetyl chloride, or by incubation with gaseous HCl, more particularly in ether as solvent or in an ether-comprising solvent. The diazidoglyoxime can be produced by reaction of dichloroglyoxime with an azide, in which case there is a chlorine/azide exchange. The azide may be, for example, sodium azide. Dimethylformamide (DMF) may be used here as a solvent. The dichloroglyoxime may be produced by reaction of glyoxime with chlorine, in ethanol as solvent, for example. The glyoxime, in turn, may be produced by reaction of glyoxal with hydroxylamine.

In one advantageous embodiment of the process, the reaction of the dichloroglyoxime with the azide takes place in a nonaqueous solvent, more particularly dimethylformamide (DMF) or N-methyl-2-pyrrolidone (NMP). The solvent with the resultant diazidoglyoxime is subsequently mixed with the ether and incubated with the gaseous HCl. The advantage of this process is that there is no need to isolate the diazidoglyoxime as an intermediate; instead, the glyoxime remains in solution. Since diazidoglyoxime is explosive, the preparation process is substantially safer as a result, and is also easier and more cost-effective to carry out, as a result of the dropping of an isolation step.

It is additionally possible, prior to step c), to evaporate the ether and the HCl and, where present, to evaporate the DMF. The evaporation of ether and HCl may possibly be facilitated by addition of $H_2O$, which then likewise requires evaporation. In the case of DMF as solvent, a mixture of dimethylammonium 5,5'-bistetrazole-1,1'-diolate and a 5,5'-bistetrazole-1,1'-diolate which comprises at least one counterion of the azide serving for the chlorine/azide exchange, and, in the case of NMP as solvent, a residue comprising 5,5'-bistetrazole-1,1'-diol, are obtained.

The stated mixture can be dissolved in $H_2O$, with subsequent addition of a hydroxylammonium salt, more particularly hydroxylammonium chloride, and so the dihydroxylammonium salt of 5,5'-bistetrazole-1,1'-diol is obtained as the precipitate.

The residue comprising 5,5'-bistetrazole-1,1'-diol may be taken up in an aqueous alkali hydroxide solution and the alkali 5,5'-bistetrazole-1,1'-diolate that precipitates may be isolated and dissolved in $H_2O$. It is possible subsequently for a hydroxylammonium salt, more particularly hydroxylammonium chloride, to be added, and so the dihydroxylammonium salt of 5,5'-bistetrazole-1,1'-diol is obtained as the precipitate.

Alternatively, in the above processes, instead of the hydroxylammonium salt, an ammonium salt, more particularly ammonium chloride, may also be added, and so the diammonium salt of 5,5'-bistetrazole-1,1'-diol is obtained as the precipitate.

The invention additionally relates to 5,5'-bistetrazole-1,2'-diol and 5,5'-bistetrazole-2,2'-diol. Both compounds are each suitable as starting material or intermediate for producing the respective dihydroxylammonium salt or diammonium salt. The invention relates, furthermore, to the dihydroxylammonium salts and diammonium salts of 5,5'-bistetrazole-1,2'-diol and 5,5'-bistetrazole-2,2'-diol.

Figure 2:
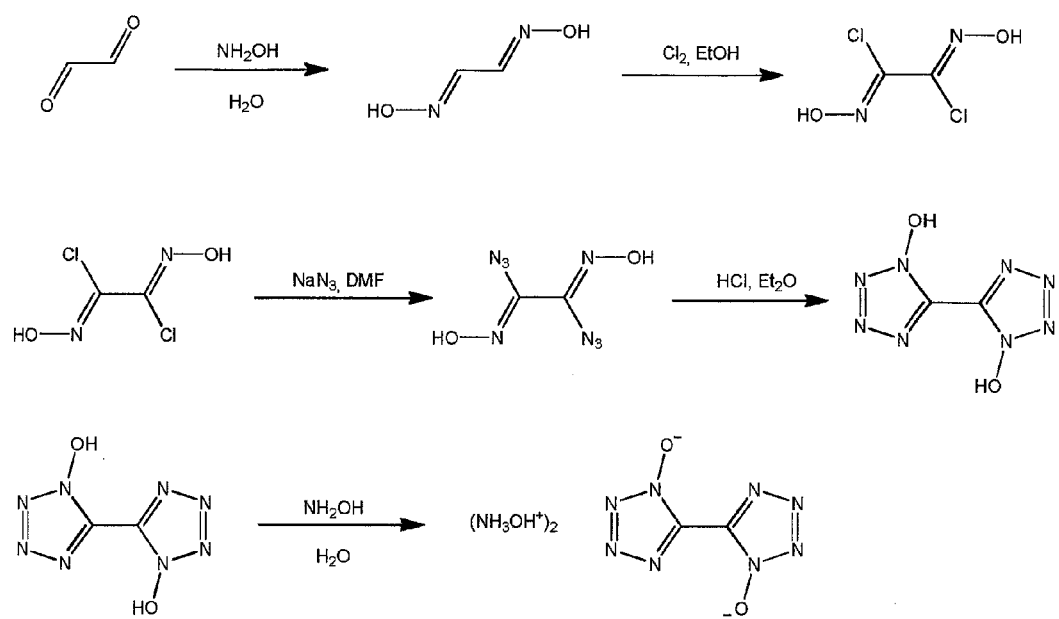
Figure 3:
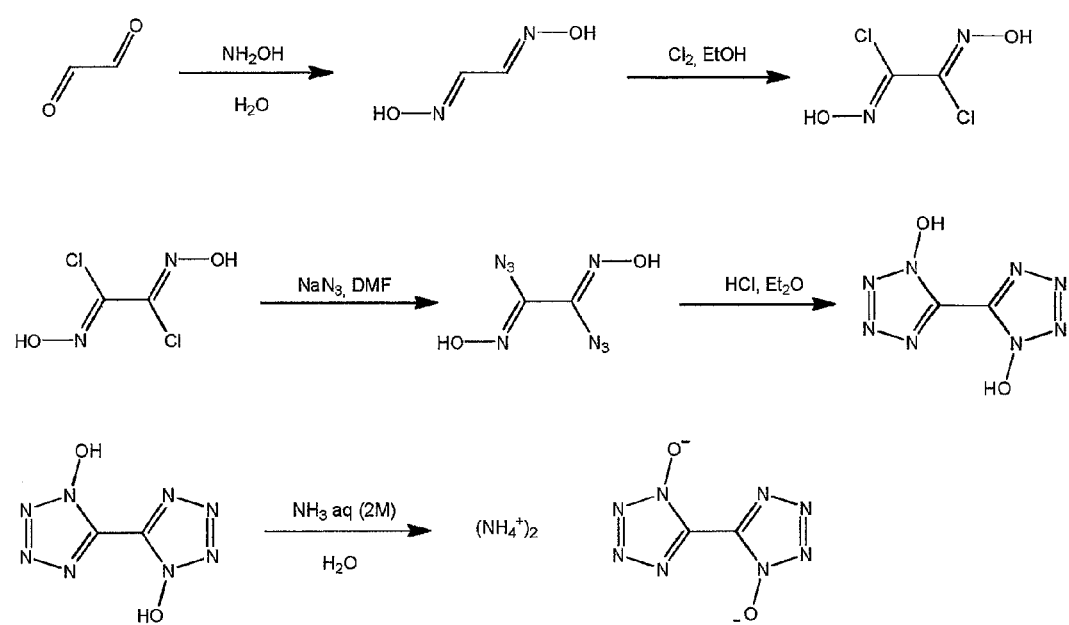

The invention is elucidated in more detail below by means of embodiments. In the figures:

FIG. 1 shows a reaction scheme of a first synthesis process for producing the dihydroxylammonium salt of 5,5'-bistetrazole-1,1'-diol, FIG. 2 shows a reaction scheme of a second synthesis process for producing the dihydroxylammonium salt of 5,5'-bistetrazole-1,1'-diol, and FIG. 3 shows a reaction scheme of a synthesis process for producing the diammonium salt of 5,5'-bistetrazole-1,1'-diol.

To carry out the first process, for the synthesis of dihydroxylammonium 5,5'-bistetrazole-1,1'-diolate according to FIG. 1, the following procedure may be adopted:

3.0 g of 5,5'-bistetrazole (21.7 mmol) are dissolved in 200 ml of water. 80.0 g of Oxone (109 mmol, 5 eq) are added to the resulting clear solution, and the resultant solution is buffered to a pH of 7 using trisodium phosphate. The mixture is stirred at room temperature for 5 hours and then acidifed with concentrated sulfuric acid. The reaction product is extracted using ether. Evaporation of the ether gives the crude product as a pale yellow solid. The solid is dissolved in methanol and recrystallized therefrom in order to remove remaining sulfates or phosphates from it. The reaction produces a mixture of 5,5'-bistetrazole-1,1'-diol, 5,5'-bistetrazole-2,2'-diol, and 5,5'-bistetrazole-1,2'-diol in a total yield of 71% (2.60 g, 15.3 mmol). In this mixture the 2,2' isomer is the principal product.

1.7 g of the isomer mixture (10 mmol) are dissolved in 20 ml of hot water. An aqueous solution of 50% (w/w) hydroxylamine (1.23 g, 20 mmol) is added to the solution. A colorless precipitate is formed immediately. The precipitate is dissolved again by heating of the mixture. In the course of slow cooling, the dihydroxylammonium salt of 5,5'-bistetrazole-1,1'-diol is precipitated. The salt is isolated by filtration. The salt is then dissolved in water and recrystallized therefrom in order to remove remaining 1,2' isomer and 2,2' isomer, both of which have a better solubility in water than does the 1,1' isomer.

The diammonium salt of 5,5'-bistetrazole-1,1'-diol may be obtained in an analogous way from the isomer mixture in solution in water. For this purpose, gaseous ammonia is introduced into the aqueous solution or an aqueous ammonia solution is added to the aqueous solution. A precipitate forms immediately, and is dissolved again by heating of the mixture. In the course of slow cooling, the diammonium salt of 5,5'-bistetrazole-1,1'-diol is precipitated. The salt is isolated by filtration and then dissolved in water and recrystallized therefrom, in order to remove remaining 1,2' isomer and 2,2' isomer, both of which have a better solubility in water than does the 1,1' isomer.

Owing to the predominant formation of the 2,2' isomer during the oxidation of the 5,5'-bistetrazole, the dihydroxylammonium salt of 5,5'-bistetrazole-1,1'-diol can be obtained in the above process only in a relatively low yield of 13% (0.31 g, 1.3 mmol). In order to obtain a higher yield, the synthesis may be carried out in accordance with the reaction scheme shown in FIG. 2. For this purpose, dichloroglyoxime is synthesized first of all, and 5,5'-bistetrazole-1,1'-diol in dihydrate form is prepared therefrom, as described in Tselinskii, I. V. et al., Russian Journal of Organic Chemistry, volume 37, No. 3, 2001, pages 430 to 436. 2.06 g (10 mmol) of the resulting dihydrate are dissolved in 50 ml of hot water. A 50% strength (w/w) hydroxylamine solution (1.32 g, 20 mmol) is added to it. On cooling of the solution to room temperature, the dihydroxylammonium salt precipitates in the form of crystals. It is isolated by filtration and dried in air. The yield is 82%.

The procedure adopted for preparing the dihydroxylammonium salt or diammonium salt of 5,5'-bistetrazole-2,2'-diol is as for the synthesis according to FIG. 1. After the precipitation of the dihydroxylammonium salt or diammonium salt of the 1,1' isomer on cooling of the mixture, the dihydroxylammonium salt or diammonium salt of 5,5'bistetrazole-2,2'-diol can be obtained by evaporating the solvent and recrystallizing the resultant residue from an ethanol/water mixture.

The synthesis of the diammonium salt of 5,5'-bistetrazole-1,1'-diol may also be carried out in accordance with the reaction scheme shown in FIG. 3. For this purpose, dichloroglyoxime is first of all synthesized and 5,5'-bistetrazole-1,1'-diol in dihydrate form is prepared from it as described in Tselinskii, I. V. et al., Russian Journal of Organic Chemistry, volume 37, No. 3, 2001, pages 430 to 436. 2.06 g (10 mmol) of the resulting dihydrate are suspended in 10 ml of a 2 M aqueous ammonia solution. Following addition of 90 ml of water, the mixture is heated to its boiling point. A clear solution is formed. On cooling of the solution to room temperature, the diammonium salt precipitates in the form of crystals. It is isolated by filtration and dried in air. The yield is 1.14 g (5.57 mmol, 56%).

Further Synthesis Processes:

TKX50: Dichloroglyoxime (785 mg, 5 mmol) is dissolved at room temperature in 10 ml of N,N'-dimethylformamide (DMF). The solution is cooled to 0° C. and $NaN_3$ (715 mg, 11 mmol) is added. The mixture is stirred at 0° C. for 40 minutes, during which NaCl precipitates and diazidoglyoxime remains in solution. The mixture is transferred to a flask in which 100 ml of diethyl ether at 0° C. have been placed, and HCl gas is introduced, the flask being cooled continually in a salt/ice bath and the temperature being not to exceed 20° C. When the temperature falls back to 0-5° C. in spite of further introduction of gas, HCl saturation of the ether phase is achieved. A precipitate which forms on introduction of HCl first undergoes agglomeration and, as HCl saturation increases, is resuspended. The flask is sealed tightly with a stopper, and stirring of the mixture is continued overnight at room temperature under a slight HCl overpressure, which forms in the flask as a result of warming to room temperature. The pressure is let off and the mixture is transferred to an open vessel, allowing diethyl ether and HCl to evaporate either overnight at room temperature or in 1-2 h at 50° C. When the major part of the ether has evaporated, 50 ml of water are added, and a clear solution is formed. The water is removed on a rotary evaporator and the DMF that is left is stripped off under a high vacuum, producing a mixture of dimethylammonium 5,5'-bistetrazole-1,1'-diolate and disodium 5,5'-bistetrazole-1,1'-diolate tetrahydrate in the form of a colorless solid. The solid is dissolved in the minimum volume of boiling water (about 10 ml) and hydroxylammonium chloride (750 mg, 10.8 mmol, 2.16 eq) is added in the form of a concentrated aqueous solution. TKX50 precipitates from the solution in a yield of 74.6% (882 mg, 3.73 mmol). It can be filtered off with suction, washed with a little cold water, and dried in the air.

ABTOX: The synthesis procedure follows the same lines as the synthesis procedure for TKX50, until the mixture of dimethylammonium 5,5'-bistetrazole-1,1'-diolate and disodium 5,5'-bistetrazole-1,1'-diolate tetrahydrate is obtained. It is again dissolved in the minimum volume of boiling water (about 10 ml), and ammonium chloride (800 mg, 15.0 mmol, 3 eq) is added in the form of a concentrated aqueous solution. In the case of ABTOX it is necessary to add a somewhat greater excess of ammonium salt, since the water-solubility of ABTOX is somewhat greater than that of TKX50. It is also necessary to reduce the volume of the solution comprising ABTOX and dimethylammonium chloride by about 30% on a rotary evaporator in order to precipitate ABTOX. It can be isolated in a yield of 78.3% (799 mg, 3.91 mmol). Similarly to TKX50, ABTOX is filtered off with suction, washed with a little cold water, and dried in the air.

TKX50: Dichloroglyoxime (785 mg, 5 mmol) is dissolved at room temperature in 10 ml of N-methyl-2-pyrrolidone (NMP). The solution is cooled to 0° C. and NaN$_3$ (715 mg, 11 mmol) is added. The mixture is stirred for 40 minutes at 0° C. NaCl is precipitated, and diazidoglyoxime remains in solution. The mixture is transferred to a flask in which 150 ml of diethyl ether have been placed, and the mixture is cooled to 0° C. in a salt/ice bath. HCl gas is introduced into the mixture, during which the temperature is not to exceed 20° C. Saturation of the ether with HCl is achieved as soon as the temperature drops to 0-5° C. again in spite of continuing introduction of HCl. A thick precipitate which has formed at the beginning of gas introduction is rapidly resuspended when HCl saturation is achieved. The flask is sealed tightly and stirring of the mixture is continued overnight at room temperature under a slight HCl overpressure, which has become established in the flask as a result of the warming to room temperature. The pressure is let off and the mixture is transferred to an open vessel, where diethyl ether and HCl can evaporate overnight at room temperature or in 1-2 h at 50° C. When the major part of the diethyl ether has evaporated, 50 ml of water are added and the solvent is removed again on a rotary evaporator. The viscous residue, which contains 5,5'-bistetrazole-1,1'-diol, NaCl, and NMP, is taken up in 20 ml of 2M NaOH, and the disodium 5,5'-bistetrazole-1,1'-diolate tetrahydrate begins to precipitate. The mixture is boiled briefly and, on cooling, there is virtually complete precipitation of the disodium 5,5'-bistetrazole-1,1'-diolate tetrahydrate. This product is filtered off with suction and dissolved in the minimum volume of boiling water (about 10 ml). Hydroxylammonium chloride (750 mg, 10.8 mmol, 2.16 eq) is added in the form of a concentrated aqueous solution. TKX50 precipitates from the solution in a yield of 85.1% (1.00 g, 4.25 mmol). It is filtered off with suction, washed with cold water, and dried in the air.

ABTOX: The synthesis procedure follows the same lines as the synthesis procedure for TKX50, until the disodium 5,5'-bistetrazole-1,1'-diolate tetrahydrate is obtained. It is again dissolved in the minimum volume of boiling water (about 10 ml), and ammonium chloride (800 mg, 15.0 mmol, 3 eq) is added in the form of a concentrated aqueous solution. In the case of ABTOX it is necessary to add a somewhat greater excess of ammonium salt, since the water-solubility of ABTOX is somewhat greater than that of TKX50. It is also necessary to reduce the volume of the solution comprising ABTOX and NaCl by about 30% on a rotary evaporator in order to precipitate ABTOX. It can be isolated in a yield of 81.3% (830 mg, 4.07 mmol). Similarly to TKX50, ABTOX is filtered off with suction, washed with a little cold water, and dried in the air.

The advantages of the further synthesis processes of TKX50 and ABTOX lie primarily in avoidance of the isolation of the diazidoglyoxime intermediate, which is highly sensitive to impact and friction. The high-sensitivity intermediate remains in solution throughout the operation, and so there are no objective dangers during the synthesis. The dimethylammonium 5,5'-bistetrazole-1,1'-diolate and disodium 5,5'-bistetrazole-1,1'-diolate tetrahydrate intermediates that are isolated here display no substantial impact sensitivity (both >40 J) and also no substantial friction sensitivity (both >360 N). A further advantage of the synthesis presented here is the saving of two reaction steps, namely the isolation of diazidoglyoxime and 5,5'-bistetrazole-1,1'-diol dihydrate, which ties in well with an industrial-scale preparation of TKX50 and ABTOX not only on financial grounds.

The invention claimed is:

1. 5,5'-Bistetrazolediol or salt thereof, wherein the 5,5'-Bistetrazolediol is 5,5'-Bistetrazole-1,2'-diol or 5,5'-Bistetrazole-2,2'-diol and the salt is dihydroxylammonium salt or diammonium salt.

2. An energetic active composition comprising a dihydroxylammonium salt or diammonium salt of 5,5'-bistetrazole-1,1'-diol, 5,5'-bistetrazole-1,2'-diol, or 5,5'-bistetrazole-2,2'-diol, or a mixture of at least two of these salts.

3. A process for preparing a dihydroxylammonium salt or diammonium salt of 5,5'-bistetrazole-1,1'-diol, 5,5'-bistetrazole-1,2'-diol, or 5,5'-bistetrazole-2,2'-diol, or a mixture of at least two of these salts, comprising the following steps:
   a) oxidizing 5,5'-bistetrazole to give a mixture of 5,5'-bistetrazole-1,1'-diol, 5,5'-bistetrazole-1,2'-diol, and 5,5'-bistetrazole-2,2'-diol, or promoting the isomerization of diazidoglyoxime to 5,5'-bistetrazole-1,1'-diol or a 5,5'-bistetra-zole-1,1'-diolate;
   b) incubating one or more reaction product from step a) with hydroxylamine, hydroxylammonium ions, ammonium ions, or ammonia in aqueous solution; and
   c) isolating the resultant precipitate.

4. The process as claimed in claim 3, wherein the oxidizing according to step a) takes place by addition of 2KHSO$_5$—KHSO$_4$—K$_2$SO$_4$ or of another inorganic or organic peroxo acid or hypofluorous acid or another oxygen transfer agent to the 5,5'-bistetrazole.

5. The process as claimed in claim 3, wherein the oxidizing takes place in an aqueous solution buffered to a pH of between 5 and 8.

6. The process as claimed in claim 3, wherein a reaction product from step a) by oxidizing of 5,5'-bistetrazole is acidified and subsequently extracted with an organic extractant and thereafter recovered from the extract, and the reaction product from step a) is subsequently optionally recrystallized and then being subjected to step b).

7. The process as claimed in claim 3, wherein, in step a), 5,5'-bistetrazole is oxidized and the aqueous solution, after the precipitation of the dihydroxylammonium salt or diammonium salt of 5,5'-bistetrazole-1,1'-diol is concentrated by evaporation, where either as a result at least the solubility product of the dihydroxyammonium salt or diammonium salt of 5,5'-bistetrazole-1,2'-diol or 5,5'-bistetrazole-2,2'-diol is exceeded, and so the dihydroxylammonium salt or diammonium salt precipitates, or the dihydroxylammonium salt or diammonium salt is obtained from the residue resulting from the evaporation by recrystallization.

8. The process as claimed in claim 3, wherein the promoting of the isomerization takes place by acylation or by incubation with gaseous HCl.

9. The process as claimed in claim 3, wherein the diazidoglyoxime is produced by reaction of dichloroglyoxime with an azide.

10. The process as claimed in claim 8, wherein the diazidoglyoxime is produced by reaction of dichloroglyoxime with an azide.

11. The process as claimed in claim 9, wherein the reaction of the dichloroglyoxime with the azide takes place in a nonaqueous solvent, the solvent with the resultant diazidoglyoxime being subsequently mixed with ether and incubated with the gaseous HCl.

12. The process as claimed in claim 10, wherein the reaction of the dichloroglyoxime with the azide takes place in a nonaqueous solvent, the solvent with the resultant diazidoglyoxime being subsequently mixed with ether and incubated with the gaseous HCl.

13. The process as claimed in claim 11, wherein before step c) ether and the HCl are evaporated off and, where present, dimethylformamide (DMF) is evaporated off, and so, in the case of DMF as solvent, a mixture of dimethylammonium 5,5'-bistetrazole-1,1'-diolate and a 5,5'-bistetrazole-1,1'-diolate which comprises at least one counterion of the azide, and in the case of N-methyl-2-pyrrolidone (NMP) as solvent a residue comprising 5,5'-bistetrazole-1,1'-diol, is obtained.

14. The process as claimed in claim 12, wherein before step c) ether and the HCl are evaporated off and, where present, dimethylformamide (DMF) is evaporated off, and so, in the case of DMF as solvent, a mixture of dimethylammonium 5,5'-bistetrazole-1,1'-diolate and a 5,5'-bistetrazole-1,1'-diolate which comprises at least one counterion of the azide, and in the case of N-methyl-2-pyrrolidone (NMP) as solvent a residue comprising 5,5'-bistetrazole-1,1'-diol, is obtained.

15. The process as claimed in claim 13, wherein the dimethylammonium 5,5'-bistetrazole-1,1'-diolate is dissolved in $H_2O$ and subsequently a hydroxylammonium salt is added, and so the dihydroxylammonium salt of 5,5'-bistetrazole-1,1'-diol is obtained as the precipitate.

16. The process as claimed in claim 14, wherein the dimethylammonium 5,5'-bistetrazole-1,1'-diolate is dissolved in $H_2O$ and subsequently a hydroxylammonium salt is added, and so the dihydroxylammonium salt of 5,5'-bistetrazole-1,1'-diol is obtained as the precipitate.

17. The process as claimed in claim 13, wherein the residue comprising 5,5'-bistetrazole-1,1'-diol is taken up in an aqueous alkali hydroxide solution and the precipitating alkali 5,5'-bistetrazole-1,1'-diolate is isolated and dissolved in $H_2O$, with subsequent addition of a hydroxylammonium salt and so the dihydroxylammonium salt of 5,5'-bistetrazole-1,1'-diol is obtained as the precipitate.

18. The process as claimed in claim 14, wherein the residue comprising 5,5'-bistetrazole-1,1'-diol is taken up in an aqueous alkali hydroxide solution and the precipitating alkali 5,5'-bistetrazole-1,1'-diolate is isolated and dissolved in $H_2O$, with subsequent addition of a hydroxylammonium salt and so the dihydroxylammonium salt of 5,5'-bistetrazole-1,1'-diol is obtained as the precipitate.

19. The process as claimed in claim 13, wherein the dimethylammonium 5,5'-bistetrazole-1,1'-diolate is dissolved in $H_2O$ and subsequently an ammonium salt is added, and so the diammonium salt of 5,5'-bistetrazole-1,1'-diol is obtained as the precipitate.

20. The process as claimed in claim 14, wherein the dimethylammonium 5,5'-bistetrazole-1,1'-diolate is dissolved in $H_2O$ and subsequently an ammonium salt is added, and so the diammonium salt of 5,5'-bistetrazole-1,1'-diol is obtained as the precipitate.

* * * * *